US009301857B2

United States Patent
Matyas et al.

(10) Patent No.: US 9,301,857 B2
(45) Date of Patent: Apr. 5, 2016

(54) SURGICAL INSTRUMENT AND METHOD OF DISASSEMBLING A TIBIAL PROSTHESIS

(71) Applicant: DEPUY (IRELAND), Cork (IE)

(72) Inventors: Aaron J. Matyas, Fort Wayne, IN (US); Stephen Bennett, Huntington, IN (US); Kyle D. Steffe, Warsaw, IN (US)

(73) Assignee: DEPUY (IRELAND) (IE)

( * ) Notice: Subject to any disclaimer, the term of this patent is extended or adjusted under 35 U.S.C. 154(b) by 0 days.

(21) Appl. No.: 14/674,461

(22) Filed: Mar. 31, 2015

(65) Prior Publication Data

US 2015/0202056 A1 Jul. 23, 2015

Related U.S. Application Data

(62) Division of application No. 13/538,617, filed on Jun. 29, 2012, now Pat. No. 9,011,458.

(51) Int. Cl.
| | |
|---|---|
| *A61B 17/92* | (2006.01) |
| *A61F 2/46* | (2006.01) |
| *A61F 2/38* | (2006.01) |
| *A61F 2/30* | (2006.01) |

(52) U.S. Cl.
CPC .............. *A61F 2/4637* (2013.01); *A61B 17/92* (2013.01); *A61F 2/30734* (2013.01); *A61F 2/389* (2013.01); *A61F 2/461* (2013.01); *A61F 2/4603* (2013.01); *A61F 2002/30738* (2013.01); *A61F 2002/4619* (2013.01); *A61F 2002/4628* (2013.01); *A61F 2002/4637* (2013.01); *A61F 2002/4641* (2013.01)

(58) Field of Classification Search
CPC ........ A61B 17/92; A61B 2/46; A61B 2/4603; A61B 2/461; A61B 2002/4619; A61B 2002/4628; A61B 2/4637; A61B 2002/4641
See application file for complete search history.

(56) References Cited

U.S. PATENT DOCUMENTS

| | | | |
|---|---|---|---|
| 2,353,623 A | 7/1944 | Saul | |
| 2,444,097 A | 6/1948 | Grant | |
| 3,997,957 A | 12/1976 | Tone et al. | |
| 5,352,227 A | 10/1994 | O'Hara | |
| 5,489,311 A * | 2/1996 | Cipolletti | A61F 2/389 623/20.34 |
| 8,435,244 B2 | 5/2013 | Meek et al. | |
| 2007/0043445 A1 | 2/2007 | Ragbir | |
| 2007/0078464 A1 | 4/2007 | Jones et al. | |
| 2008/0275457 A1* | 11/2008 | Meek | A61B 17/88 606/99 |
| 2011/0107574 A1 | 5/2011 | Melanson | |
| 2013/0289629 A1 | 10/2013 | Miller | |

FOREIGN PATENT DOCUMENTS

EP 1106148 A1 6/2001

OTHER PUBLICATIONS

European Search Report, European Application No. 13173837.9-1654, Sep. 17, 2013, 7 pages.

* cited by examiner

*Primary Examiner* — Larry E Waggle, Jr.
(74) *Attorney, Agent, or Firm* — Barnes & Thornburg, LLP

(57) ABSTRACT

An orthopaedic surgical instrument and method includes securing an anchor to a tibial prosthetic component implanted in a proximal end of a patient's tibia, moving a separator posteriorly toward the anchor to position a tip of the separator between a lower side of the tibial tray and an upper end of the tibial sleeve, advancing the separator from anterior to posterior between the lower side of the tibial tray and the upper end of the tibial sleeve to detach the tibial tray from the tibial sleeve, and removing the tibial tray from the proximal end of the patient's tibia. The tibial prosthetic component includes a tibial tray and a tibial sleeve secured to the tibial tray.

6 Claims, 9 Drawing Sheets

SURGICAL INSTRUMENT AND METHOD OF DISASSEMBLING A TIBIAL PROSTHESIS

This application is a divisional application of, and claims priority to U.S. patent application Ser. No. 13/538,617, which was filed on Jun. 29, 2012 and is expressly incorporated herein by reference.

TECHNICAL FIELD

The present disclosure relates generally to orthopaedic surgical instruments and, more particularly, to surgical instruments used in the assembly and disassembly of orthopaedic prosthetic components.

BACKGROUND

Joint arthroplasty is a well-known surgical procedure by which a diseased and/or damaged natural joint is replaced by a prosthetic joint. For example, in a total knee arthroplasty surgical procedure, a patient's natural knee joint is partially or totally replaced by a prosthetic knee joint or knee prosthesis. A typical knee prosthesis includes a tibial component, a femoral component, and an insert or bearing component positioned between the tibial component and the femoral component. The tibial component generally includes a platform or plate having a stem extending distally therefrom, and the femoral component generally includes a pair of spaced apart condylar elements, which include surfaces that articulate with corresponding surfaces of the polymer bearing. The stem of the tibial tray is configured to be implanted in a surgically-prepared medullary canal of the patient's tibia, and the femoral component is configured to be coupled to a surgically-prepared distal end of a patient's femur From time to time, a revision knee surgery may need to be performed on a patient. In such a revision knee surgery, the previously-implanted knee prosthesis is surgically removed and a replacement knee prosthesis is implanted. In some revision knee surgeries, all of the components of the previously-implanted knee prosthesis, including, for example, the tibial component, the femoral component, and the polymer bearing component, may be surgically removed. In other revision knee surgeries, only part of the previously-implanted knee prosthesis may be removed and replaced.

During a revision knee surgery, the orthopaedic surgeon typically uses a variety of different orthopaedic surgical instruments such as, for example, cutting blocks, surgical reamers, drill guides, prosthetic trials, and other surgical instruments to prepare the patient's bones to receive the knee prosthesis.

SUMMARY

According to one aspect of the disclosure, an orthopaedic surgical instrument is disclosed. The orthopaedic surgical instrument includes an anchor having a longitudinal axis, and a shaft coupled to the anchor. The shaft has a longitudinal axis extending orthogonal to the longitudinal axis of the anchor. The orthopaedic surgical instrument also includes a separator coupled to the shaft. The separator has a pair of arms and a slot defined therebetween. The separator is configured to move along the longitudinal axis of the shaft between a first position in which the anchor is spaced apart from the slot of the separator and a second position in which the anchor is received in the slot defined between the pair of arms.

In some embodiments, each arm of the separator may include a top surface, a bottom surface, and a tapered surface extending between the top surface and the bottom surface. Additionally, in some embodiments, the separator may include a body secured to the pair of arms, and the shaft may be positioned in a bore defined in the body.

In some embodiments, the orthopaedic surgical instrument may include a collar rotatively coupled to the shaft, and the collar may be operable to move the separator between the first position and the second position. Additionally, in some embodiments, the shaft may have a plurality of external threads formed thereon, and the bore in the body may be defined by a substantially smooth inner surface that engages the shaft. In some embodiments, the collar may include an opening defined in a first end thereof and an inner wall that extends inwardly from the opening, and the inner wall of the collar may have a plurality of internal threads formed thereon. The plurality of internal threads may be engaged with a number of the external threads of the shaft.

In some embodiments, the first end of the collar may be engaged with the body such that rotation of the collar in a first direction causes the separator to advance between the first position and the second position. In some embodiments, the body may be positioned between the anchor and the collar.

Additionally, in some embodiments, the orthopaedic surgical instrument may include a handle configured to rotate the collar about the longitudinal axis of the shaft to advance the separator between the first position and the second position. The handle may have a socket defined therein. The collar may have a shank sized to be positioned in the socket defined in the handle.

In some embodiments, the anchor may include a cylindrical shaft extending along the longitudinal axis of the anchor. The cylindrical shaft may be sized and shaped to be positioned in a bore defined in a tibial tray. In some embodiments, the orthopaedic surgical instrument may include a stabilizer including a rod received in a bore defined in the anchor.

According to another aspect, an orthopaedic surgical instrument includes an anchor including a frustoconical first body and a cylindrical second body extending downwardly from the frustoconical first body, and a shaft secured to the anchor. The shaft has an externally-threaded outer surface and a longitudinal axis. The orthopaedic surgical instrument includes a housing having an internally-threaded inner surface engaged with externally-threaded outer surface of the shaft, and the housing is configured to rotate about the longitudinal axis of the shaft. The orthopaedic surgical instrument also includes a separator including a mounting body positioned between the anchor and the housing and a pair of arms having a slot defined therebetween. The housing is engaged with the mounting body such that rotation of the housing about the longitudinal axis causes the separator to move between a first position in which the anchor is spaced apart from the slot of the separator and a second position in which the anchor is received in the slot defined between the pair of arms.

In some embodiments, each arm of the separator may include a tapered surface. In some embodiments, the anchor may include a base secured to the shaft, and the first body may be secured to a lower end of the base.

According to another aspect, a method of performing an orthopaedic surgical procedure is disclosed. The method includes securing an anchor to a tibial prosthetic component implanted in a proximal end of a patient's tibia. The tibial prosthetic component includes a tibial tray and a tibial sleeve secured to the tibial tray. The method also includes moving a separator posteriorly toward the anchor to position a tip of the separator between a lower side of the tibial tray and an upper end of the tibial sleeve, advancing the separator from anterior to posterior between the lower side of the tibial tray and the upper end of the tibial sleeve to detach the tibial tray from the tibial sleeve, and removing the tibial tray from the proximal end of the patient's tibia.

In some embodiments, the method may further include positioning a cylindrical body of the anchor in an opening defined in the tibial tray. Additionally, in some embodiments, moving the separator toward the anchor includes sliding the separator along a shaft secured to the anchor.

In some embodiments, a collar may be threaded onto the shaft. In some embodiments, sliding the separator along the shaft may include rotating the collar on the shaft to advance the collar along the shaft and engaging the separator with the collar as the collar is advanced along the shaft.

In some embodiments, the method may include engaging the collar with a handle, and operating the handle to rotate the collar on the shaft.

In some embodiments, advancing the separator may include positioning a wedge of the separator between the tibial tray and the tibial sleeve.

BRIEF DESCRIPTION OF THE DRAWINGS

The detailed description particularly refers to the following figures, in which.

DETAILED DESCRIPTION OF THE DRAWINGS

Figure 1:
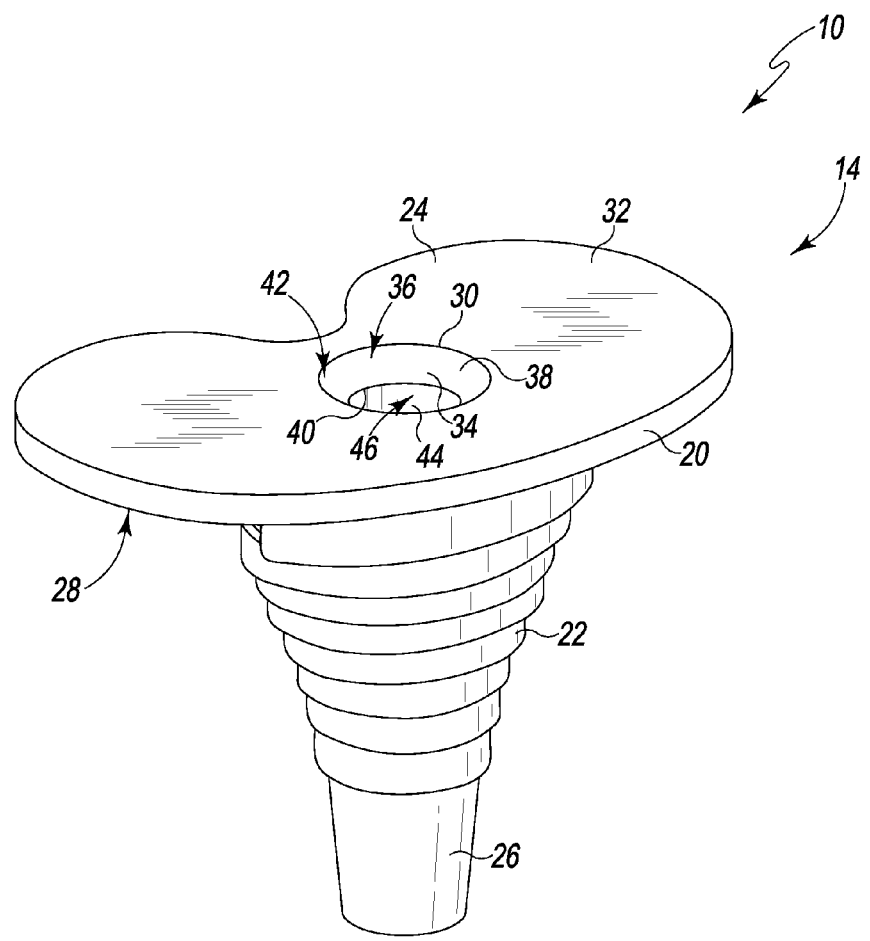
FIG. 1 is a perspective view of a prosthetic tibial component of a knee prosthesis.

While the concepts of the present disclosure are susceptible to various modifications and alternative forms, specific exemplary embodiments thereof have been shown by way of example in the drawings and will herein be described in detail. It should be understood, however, that there is no intent to limit the concepts of the present disclosure to the particular forms disclosed, but on the contrary, the intention is to cover all modifications, equivalents, and alternatives falling within the spirit and scope of the invention as defined by the appended claims.

Terms representing anatomical references, such as anterior, posterior, medial, lateral, superior, inferior, etcetera, may be used throughout the specification in reference to the orthopaedic implants and surgical instruments described herein as well as in reference to the patient's natural anatomy. Such terms have well-understood meanings in both the study of anatomy and the field of orthopaedics. Use of such anatomical reference terms in the written description and claims is intended to be consistent with their well-understood meanings unless noted otherwise.

Figure 2:
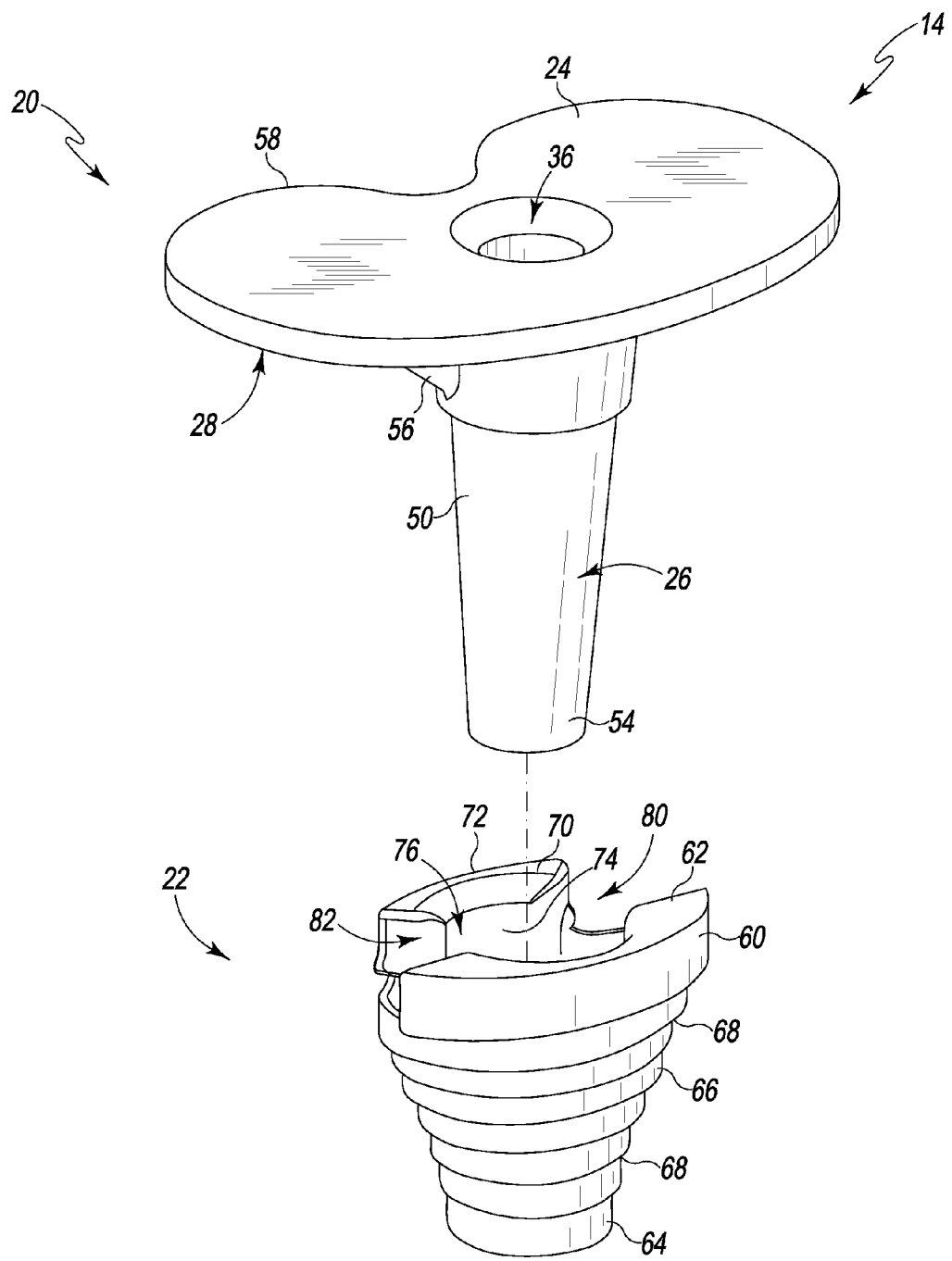
FIG. 2 is an exploded perspective view of the tibial component of FIG. 1.

Referring now to FIGS. 1-4, a knee prosthesis 10 and a surgical instrument 12 are shown. As shown in FIGS. 1 and 2, the knee prosthesis 10 includes a prosthetic tibial component 14 that is configured to be implanted in a surgically-prepared proximal end 16 of a patient's tibia 18 (see FIG. 5). As described in greater detail below in reference to FIGS. 5-8, the surgical instrument 12 may be used in a joint replacement procedure to remove the tibial component 14 from the patient's tibia 18. It should be appreciated that although the surgical instrument 12 is herein described in regard to the performance of a total knee replacement procedure, certain of the concepts associated with the instrument 12 may be utilized in association with replacement procedures at numerous other joint locations throughout the body.

As shown in FIG. 1, the tibial component 14 of the knee prosthesis 10 includes a tibial tray 20 and a sleeve 22. The tibial tray 20 is configured to be coupled to a tibial bearing component (not shown) of the knee prosthesis 10. The tibial tray 20 includes a platform 24 and a fixation member, such as an elongated stem 26, extending away from a distal side 28 of the platform 24. An opening 30 is defined in a proximal surface 32 of the platform 24, and the tibial tray 20 includes an inner wall 34 that extends distally from the opening 30. The inner wall 34 defines a bore 36 extending through the platform 24 into the stem 26. The bore 36 is sized and shaped to receive a stem (not shown) of the tibial bearing component of the knee prosthesis 10.

The inner wall 34 of the tibial tray 20 has a tapered surface 38 that extends distally from the opening 30 in the proximal surface 32 to a distal edge 40. As shown in FIG. 1, the tapered surface 38 defines a proximal section 42 of the bore 36. The inner wall 34 also includes a cylindrical surface 44 that is connected to the tapered surface 38 at the distal edge 40 thereof. The cylindrical surface 44 extends distally from the edge 40 to define a distal section 46 of the bore 36. It should be appreciated that in other embodiments the inner wall 34 may include a single tapered surface, a single cylindrical surface, or additional surfaces to define the bore 36.

As shown in FIG. 2, the elongated stem 26 of the tibial tray 20 has a body 50 extending from a proximal end attached to the platform 24 to a distal end 54. The body 50 is tapered from a widest dimension at the proximal end to a most narrow dimension at the distal end 54. In the illustrative embodiment, the body 50 has a Morse taper. The distal end 54 of the stem 26 is configured to be secured to an extension (not shown).

The tibial tray 20 also includes a pair of keels 56 extending from the distal side 28 of the platform 24. In the illustrative embodiment, each keel 56 extends outwardly from the stem 26 and toward the posterior side 58 of the platform 24. It should be appreciated that in other embodiments the keels may have other geometric relationships and the tibial tray 20 may include additional or fewer keels.

As described above, the tibial component 14 also includes a sleeve 22, which is configured to be secured to the tibial tray 20. The sleeve 22 has a body 60 that extends from a proximal end 62 to a distal end 64. As shown in FIG. 2, the body 60 is tapered from a widest dimension at the proximal end 62 to a most narrow dimension at the distal end 64. In the illustrative embodiment, the body 60 has a stepped or terraced outer surface 66 including a plurality of steps 68. The outer surface 66 tapers with each step 68 from the proximal end 62 to the distal end 64.

The sleeve 22 has an opening 70 defined in a proximal surface 72 of the body 60, and an inner wall 74 extends distally from the opening 70 to define an interior passageway 76. The passageway 76 is sized and shaped to receive the stem 26 of the tibial tray 20 when the sleeve 22 is assembled with the tray 20. The inner wall 74 tapers from a largest diameter at the proximal surface 72 to a smallest diameter at the distal end 64. In the illustrative embodiment, the inner wall 74 of the sleeve 22 has a Morse taper that matches the Morse taper of the stem 26 of the tibial tray 20.

The sleeve 22 also includes a pair of relief slots 80, 82 that extend inwardly from the outer surface 66 of the body 60. As shown in FIG. 2, the slots 80, 82 open into the passageway 76. The slots 80, 82 are sized to receive the keels 56 when the sleeve 22 is secured to the tibial tray 20.

Figure 6:
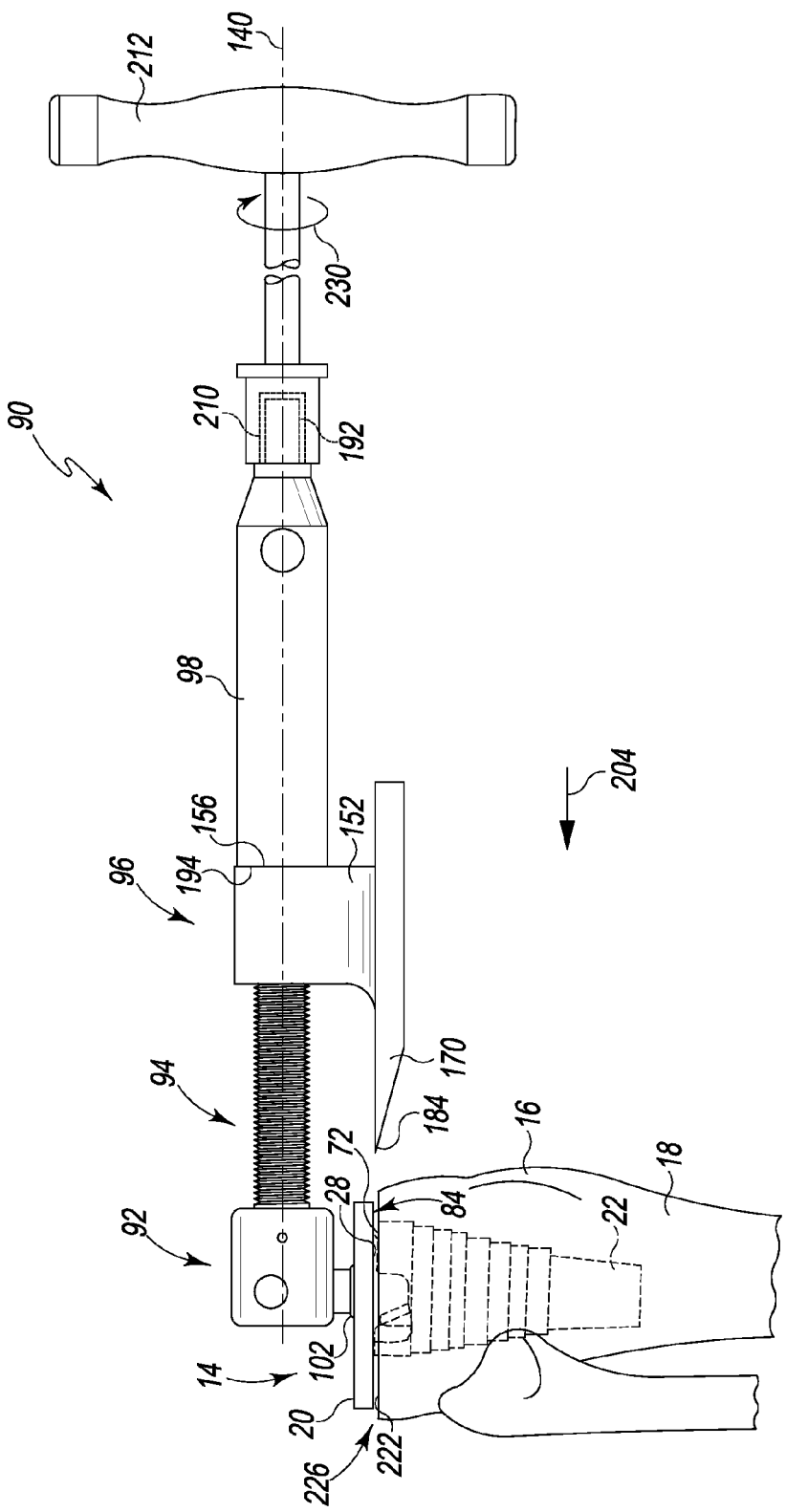
FIG. 6 is an elevation view of the orthopaedic surgical instrument of FIG. 3 attached to the implanted tibial component with a separator of the orthopaedic surgical instrument spaced apart from the implanted tibial component.

When the sleeve 22 is assembled with the tibial tray 20, the stem 26 of the tibial tray 20 is received in the passageway 76 of the sleeve 22, and the keels 56 are positioned in the slots 80, 82. The stem 26 engages the inner wall 74 of the sleeve 22, thereby creating a frictional lock between the tibial tray 20 and the sleeve 22. The frictional lock prevents relative rotation and longitudinal movement between the tibial tray 20 and the sleeve 22, thereby forming the tibial component 14. As shown in FIG. 6, a slot 84 is defined between the distal side 28 of the tibial tray 20 and the proximal surface 72 of the sleeve 22.

The tibial tray 20 and the sleeve 22 are formed of materials suitable for prosthetic components. Such materials include titanium alloys, cobalt chromium alloys, or other metallic alloys. It should be appreciated that in other embodiments other metallic materials may be used.

Figure 3:
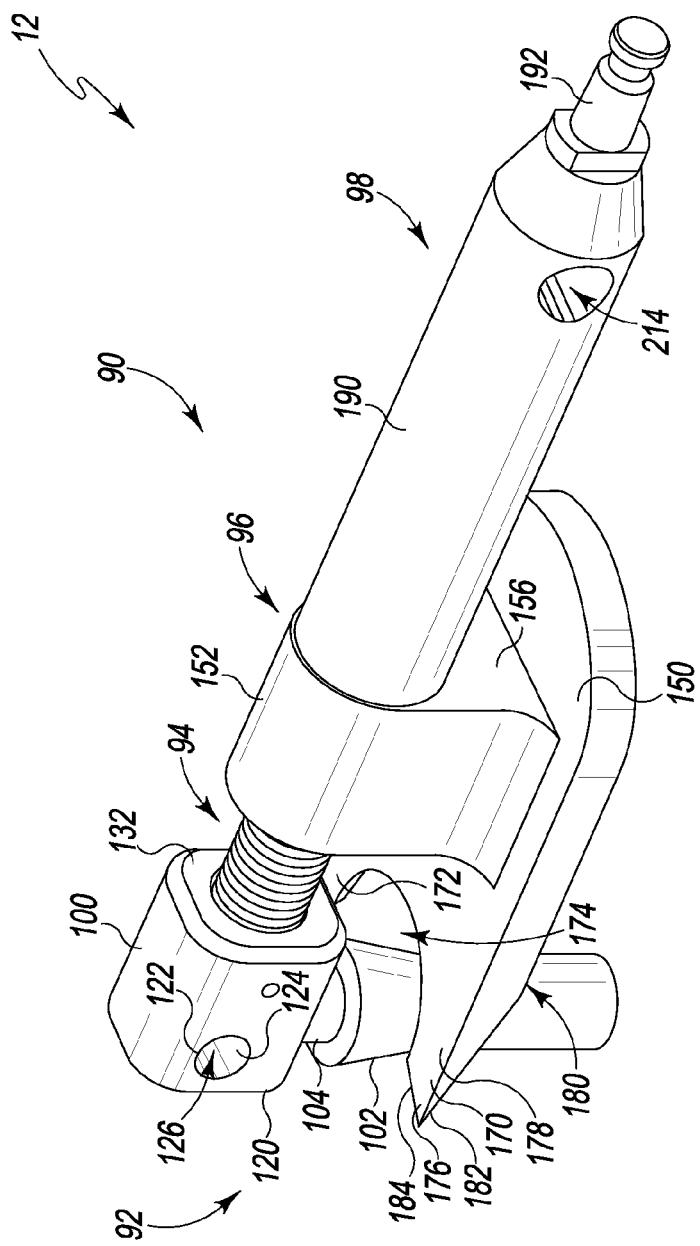
FIG. 3 is a perspective view of one embodiment of an orthopaedic surgical instrument for use in disassembling the tibial component of FIG. 1.
Figure 4:
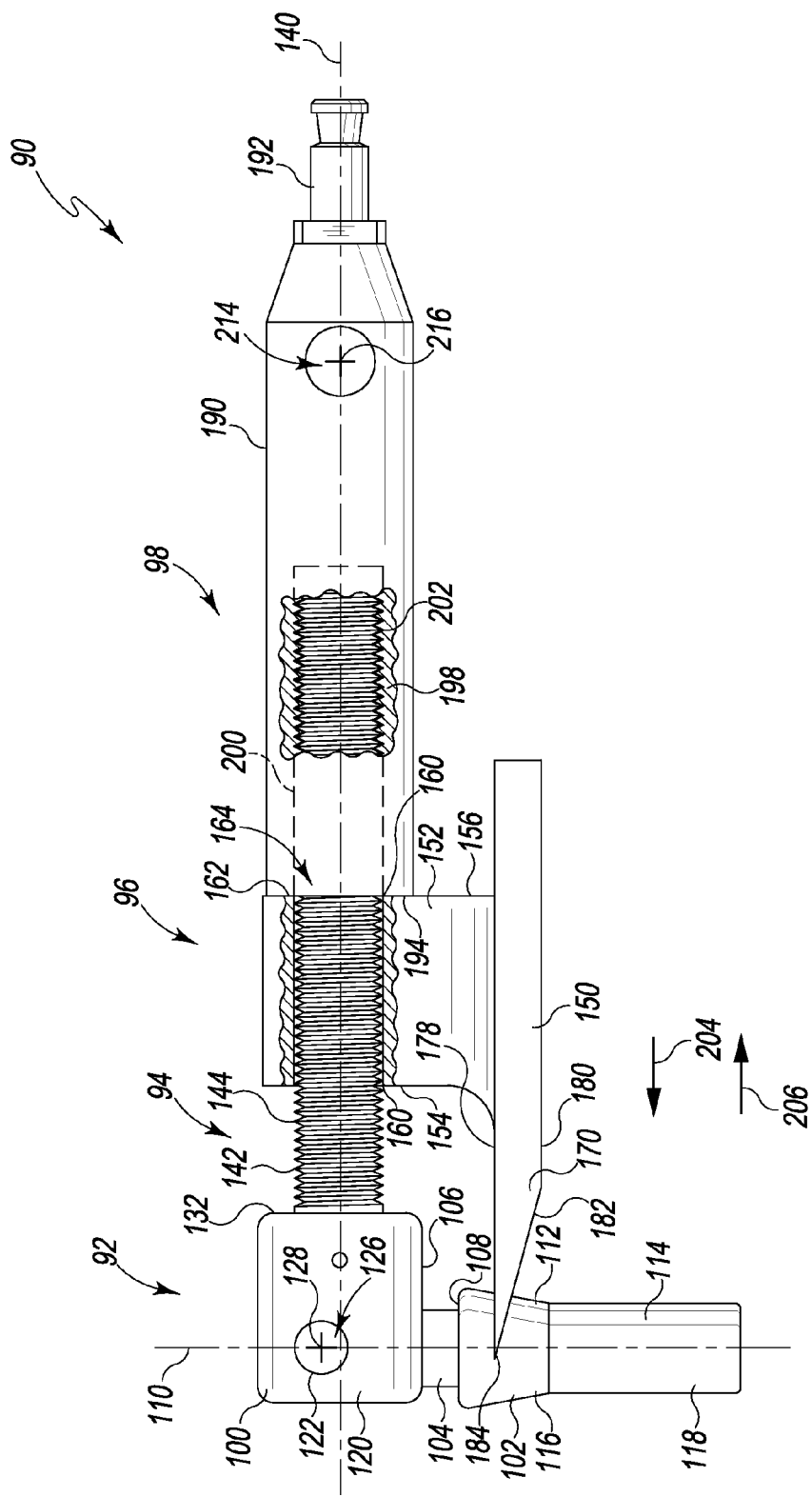
FIG. 4 is a partial cross-section, elevation view of the orthopaedic surgical instrument of FIG. 3.

Referring now to FIGS. 3 and 4, the surgical instrument 12 may be used in an orthopaedic surgical procedure during the removal of the tibial component 14 from the patient's tibia 18. In the illustrative embodiment, the surgical instrument 12 is a disassembly instrument 90 configured to separate the tibial tray 20 from the sleeve 22 and facilitate the removal of the tibial component 14. The instrument 90 includes an anchor 92 configured to be secured to the tibial tray 20 and a shaft 94 extending outwardly from the anchor 92. The instrument 90 also includes a separator tool 96 configured to move relative to the anchor 92 and engage the tibial component 14 to separate the tibial tray 20 from the sleeve 22. An actuation collar 98 is attached to the shaft 94 and is operable to move the separator tool 96 along the shaft 94, as described in greater detail below. In the illustrative embodiment, the components of the instrument 90 are formed from a metallic material such as, for example, steel, titanium alloy, cobalt chromium alloy, and so forth. It should be appreciated that in other embodiments the components may be formed from a hard polymeric material.

The anchor 92 of the instrument 90 includes a base 100 and an engagement arm 102 configured to be positioned in the bore 36 defined in the tibial tray 20. In the illustrative embodiment, the engagement arm 102 is secured to the base 100 via a connecting rod 104. As shown in FIGS. 3 and 4, the connecting rod 104 extends between a bottom surface 106 of the base 100 and an upper surface 108 of the engagement arm 102. It should be appreciated that in other embodiments the engagement arm 102 may be secured directly to the base 100.

The engagement arm 102 has a longitudinal axis 110 that extends through an upper body 112 secured to the connecting rod 104 and a lower body 114 positioned below the upper body 112. In the illustrative embodiment, the upper body 112 has a frustoconical outer surface 116 shaped to match the tapered surface 38 that defines the proximal section 42 of the bore 36. When the anchor 92 is secured to the tibial tray 20, the upper body 112 of the arm 102 is received in the proximal section 42 of the bore 36 of the tibial tray 20. Additionally, the lower body 114 of the engagement arm 102 is received in the distal section 46 of the bore 36 when the anchor 92 is secured to the tibial tray 20. Similar to the upper body 112, the lower body 114 has a cylindrical outer surface 118 shaped to match the cylindrical surface 44 that defines the distal section 46 of the bore 36. It should be appreciated that in other embodiments the engagement arm 102 may be detachable from the base 100. In that way, the instrument 90 may include multiple engagement arms, and each engagement arm may be sized to be used with a different size of tibial tray.

The base 100 of the anchor 92 includes a pair of side surfaces 120 that extend upwardly from the bottom surface 106. An opening 122 is defined in each side surface 120, and an inner wall 124 extends between the openings 122 to define a bore 126 through the base 100. As shown in FIG. 4, the bore 126 has a longitudinal axis 128 that extends transverse to the longitudinal axis 110 of the engagement arm 102. The bore 126 is sized to receive a stabilizer rod 130 (see FIG. 7), which may be used by the surgeon to support the instrument 90 on the patient's tibia 18.

The base 100 of the anchor 92 includes another side surface 132 that extends upwardly from the bottom surface 106 between the side surfaces 120. As shown in FIGS. 3 and 4, the shaft 94 of the instrument 90 extends outwardly from the side surface 132. In the illustrative embodiment, the shaft 94 has a longitudinal axis 140 that extends orthogonal to the longitudinal axis 110 of the engagement arm 102. The shaft 94 has a cylindrical outer surface 142 that has a plurality of external threads 144 formed thereon.

As described above, the instrument 90 also includes a separator tool 96 that is configured to move relative to the anchor 92. The separator tool 96 includes a plate 150 and a body 152 extending upwardly from the plate 150. As shown in FIGS. 3 and 4, the body 152 of the separator tool 96 is mounted on the shaft 94. The body 152 has a side surface 154 that faces the side surface 132 of the base 100 and another side surface 156 that is positioned opposite the side surface 154. Each surface 154, 156 of the body 152 has an opening 160 defined therein. A cylindrical inner wall 162 extends between the openings 160 to define a passageway 164 through the body 152. As shown in FIG. 4, the shaft 94 extends through the passageway 164 of the body 152. The inner wall 162 of the body 152 is substantially smooth such that the separator tool 96 is permitted to slide along the threads 144 of the shaft 94.

The separator tool 96 also includes a pair of arms 170, 172 that extend outwardly from the plate 150. As shown in FIG. 3, an opening 174 is defined between the arms 170, 172, which is sized to receive the proximal end of the stem 26 and the keels 56 of the tibial tray 20, as described in greater detail below. Each of the arms 170, 172 includes a wedge 176 that is defined by a substantially planar top surface 178, a substantially planar bottom surface 180, and a tapered surface 182 extending between the surfaces 178, 180. Each of the arms 170, 172 has a tip 184 formed by the intersection of the top surface 178 and the tapered surface 182.

As described above, the instrument 90 also includes an actuation collar 98 that is operable to move the separator tool 96 along the shaft 94. As shown in FIGS. 3 and 4, the collar 98 includes a housing 190 and a shank 192 extending outwardly from the housing 190. The housing 190 has a surface 194 that is configured to engage the side surface 156 of the separator tool 96. An opening (not shown) is defined in the surface 194 of the housing 190, and a cylindrical inner wall 198 extends inwardly from the opening to define an aperture 200 in the housing 190.

The collar 98 has a plurality of internal threads 202 formed on the inner wall 198 of the housing 190, and the internal threads 202 correspond to the external threads 144 of the shaft 94. As shown in FIG. 4, the internal threads 202 of the collar 98 engage the external threads 144 such that rotation of the collar 98 about the longitudinal axis 140 of the shaft 94 causes the collar 98 to move along the shaft 94. In the illustrative embodiment, clockwise rotation of the collar 98 advances the collar 98 along the shaft 94 toward the anchor 92, as indicated by arrow 204 in FIG. 4; counter-clockwise rotation of the collar 98 moves the collar 98 away from the anchor 92, as indicated by arrow 206 in FIG. 4.

When the collar 98 is rotated clockwise, the collar 98 is advanced into contact with the separator tool 96. The surface 194 of the collar 98 engages the side surface 156 of the body 152 such that continued movement of the collar 98 causes the separator tool 96 to move toward the anchor 92. In that way, the collar 98 is operable to move the separator tool 96 along the shaft 94. The collar 98 may be utilized to move the anchor 92 between a position in which the anchor 92 is spaced apart from the opening 174 defined between the arms 170, 172 of the separator tool 96 and, as shown in FIG. 3, another position in which the anchor 92 is positioned in the opening 174.

As described above, the collar 98 of the instrument 90 also includes a shank 192 that extends outwardly from the housing 190. The shank 192 is sized and shaped to be received in a corresponding socket 210 of a T-handle 212 (see FIG. 8), which may be operated by a surgeon or other user to rotate the collar 98 about the longitudinal axis 140. The shank 192 may also be sized to receive a socket of a power tool (not shown) such that the collar 98 may be rotated by an electric motor. It should also be appreciated that the collar 98 may also be rotated by hand, and, in other embodiments, the housing 190 of the collar 98 may include a grip sized to receive a hand of a surgeon.

As shown in FIG. 4, the collar 98 of the instrument 90 has a bore 214 defined in the housing 190. The bore 214 has a longitudinal axis 216 that extends transverse to the longitudinal axis 140 of the shaft 94. The bore 214 is sized to receive a stabilizer rod 218 (see FIG. 7), which may be used by the surgeon to support the instrument 90 on the patient's tibia 18.

In operation, the disassembly instrument 90 may be used during an orthopaedic surgical procedure to facilitate the removal of a previously-implanted tibial component 14. To do so, as shown in FIGS. 5-8, the surgeon may remove bone cement from between the tibial tray 20 of the tibial component 14 and the proximal end 16 of the patient's tibia 18. The surgeon may utilize the instrument 90 to separate the tibial tray 20 from the sleeve 22 and remove the tibial tray 20 from the patient's tibia 18. Thereafter, the surgeon may remove the sleeve 22 from the patient's tibia 18 before preparing the patient's tibia 18 to receive a replacement prosthetic tibial component.

Figure 5:
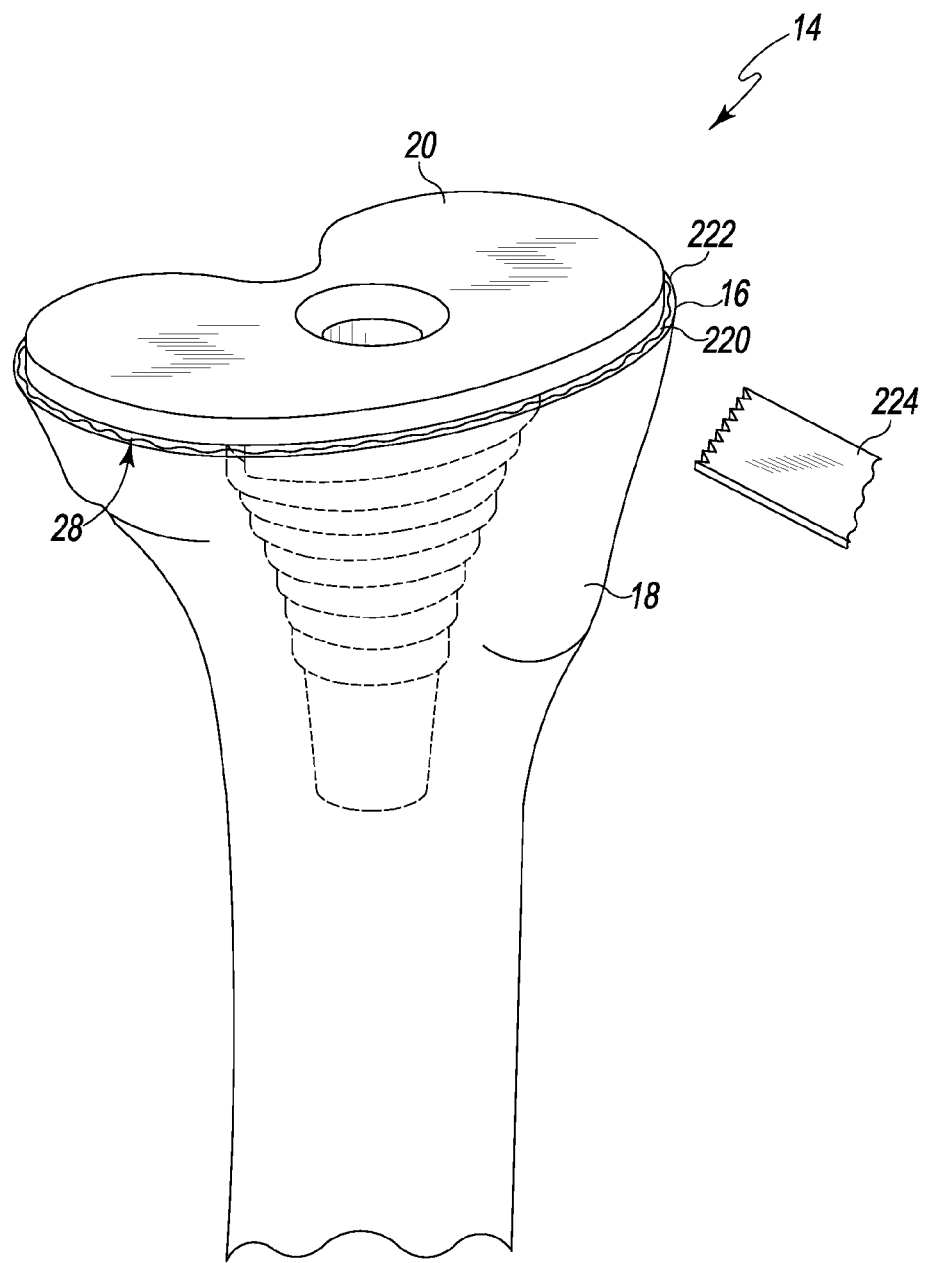
FIG. 5 is a perspective view of the tibial component of FIG. 1 implanted in a proximal end of a tibia of a patient.

As shown in FIG. 5, the tibial component 14 is implanted in the proximal end 16 of the patient's tibia 18. In the illustrative embodiment, bone cement 220 is positioned between the distal side 28 of the tibial tray 20 and the proximal surface 222 of the patient's tibia 18. The surgeon may utilize a surgical saw 224 to remove a portion of the bone cement 220 and/or bone 18 from the area between the tray 20 and the surface 222. In that way, a gap 226 is defined between patient's tibia 18 and the distal side 28 of the tibial tray 20, as shown in FIG. 6.

The surgeon may utilize the disassembly instrument 90 to separate the tibial tray 20 from the sleeve 22. To do so, the surgeon inserts the engagement arm 102 of the anchor 92 into the bore 36 defined in the tibial tray 20 of the tibial component 14, as shown in FIG. 6. When properly positioned, the upper body 112 of the engagement arm 102 is received in the proximal section 42 of the bore 36 and the lower body 114 of the engagement arm 102 is received in the distal section 46. As shown in FIG. 6, the shaft 94 extends anteriorly from the patient's tibia 18.

The separator tool 96 of the instrument 90 is initially spaced apart from the anchor 92 and the tibial component 14 before being advanced into engagement with the tibial component 14. To move the separator tool 96 toward the tibial component 14, the surgeon may attach a handle 212 to the actuation collar 98. As shown in FIG. 6, the handle 212 has a socket 210 defined therein that is sized to receive the shank 192. The surgeon may rotate the handle 212 about the longitudinal axis 140 in the direction indicated by arrow 230, thereby rotating the actuation collar 98. As the collar 98 is rotated, the collar 98 is advanced into contact with the separator tool 96. The surface 194 of the collar 98 engages the side surface 156 of the body 152 to move the separator tool 96 along the shaft 94 in the direction indicated by arrow 204. In that way, the separator tool 96 is advanced toward the anchor 92 and the tibial component 14 implanted in the patient's tibia 18. It should be appreciated that in other embodiments the surgeon may rotate the collar 98 by, for example, gripping the housing 190.

Figure 7:
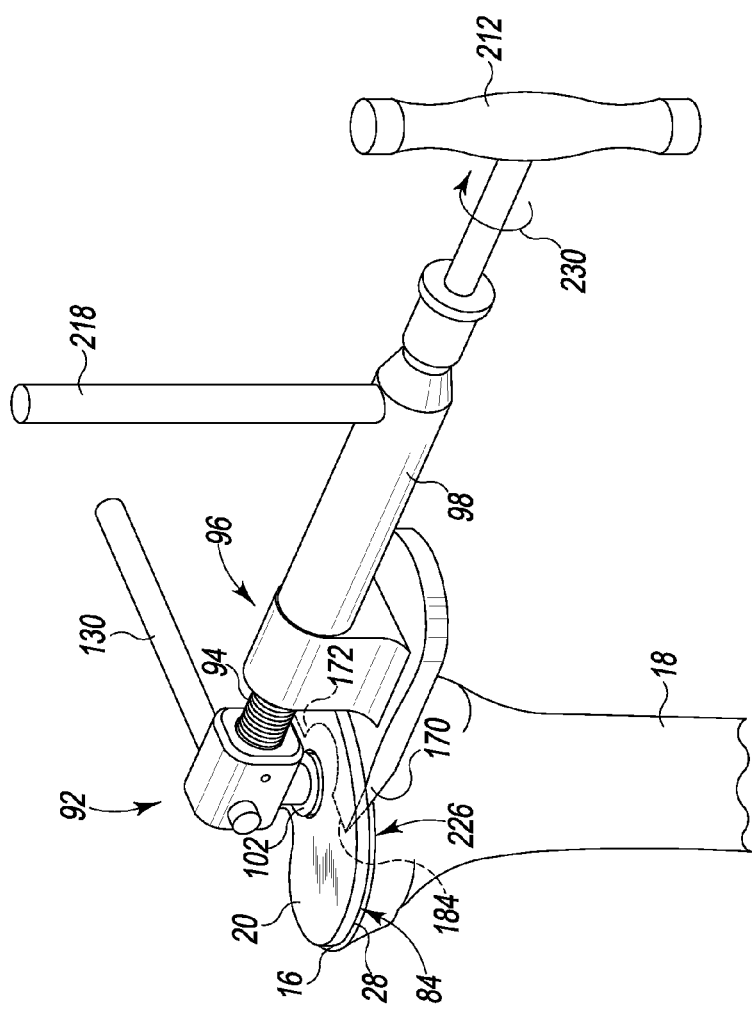
FIG. 7 is a perspective view similar to FIG. 5 showing the separator of the orthopaedic surgical instrument engaged with the implanted tibial component.
Figure 8:
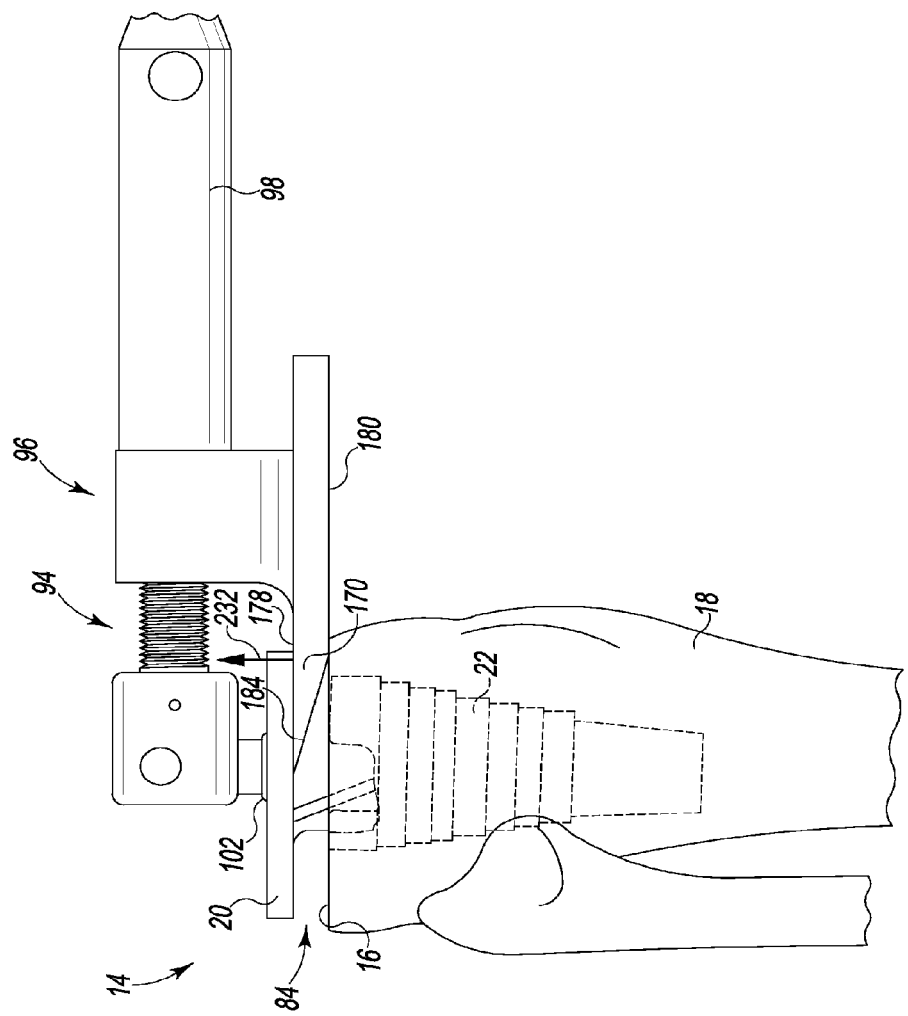
FIG. 8 is an elevation view similar to FIG. 6 showing the separator in the position of FIG. 7.

The surgeon may continue to rotate the handle 212 to move the separator tool 96 posteriorly into engagement with the tibial component 14 and the proximal end 16 of the patient's tibia 18. As shown in FIG. 7, the tip 184 of each of the arms 170, 172 is advanced into the gap 226 formed between the patient's tibia 18 and the distal side 28 of the tibial tray 20 and further into the slot 84 defined between the distal side 28 of the tibial tray 20 and the proximal surface 72 of the sleeve 22. The surgeon may use the stabilizer rods 130, 218 to support the instrument 90 on the patient's tibia 18.

When the tips 184 of the arms 170, 172 are positioned in the slot 84, the surgeon may apply additional force to the handle 212 to continue to rotate the handle 212 about the axis 140. The surgeon may also apply additional force using the stabilizer rod 218. In doing so, the wedges 176 of the arms 170, 172 exert an upward force on the tibial tray 20, as indicated by arrow 232 in FIG. 8. As the separator tool 96 is advanced anterior to posterior, the tapered surfaces 182 of the arms 170, 172 slide along the bone 18 and the proximal end 62 of the sleeve 22, thereby moving the tibial tray 20 upward while the sleeve 22 remains in position within the patient's tibia 18. In that way, the frictional lock between the sleeve 22 and the tray 20 may be broken such that the tibial tray 20 may be separator from the sleeve 22.

The surgeon may continue moving the separator tool 96 posteriorly until the stem 26 and the keels 56 of the tibial tray 20 are positioned in the opening 174 defined between the arms 170, 172. In that position, the planar top surface 178 of the arms 170, 172 is engaged with the distal side 28 of the tibial tray 20 and the planar bottom surface 180 of the arms 170, 172 is engaged with the proximal surface 72 of the sleeve 22. The surgeon may then manually remove the tibial tray 20 from the sleeve 22 and hence from the patient's tibia 18. If the surgeon is unable to manually remove the tibial tray 20, the surgeon may use a mallet (not shown) or other surgical tool to complete the separation of the tibial tray 20 from the sleeve 22 and the patient's tibia 18.

Once the tibial tray 20 is removed, the surgeon may the remove the sleeve 22 by using a separate removal tool. The surgeon may then surgically prepare the proximal end 16 of the patient's tibia to receive a replacement tibial component.

Figure 9:
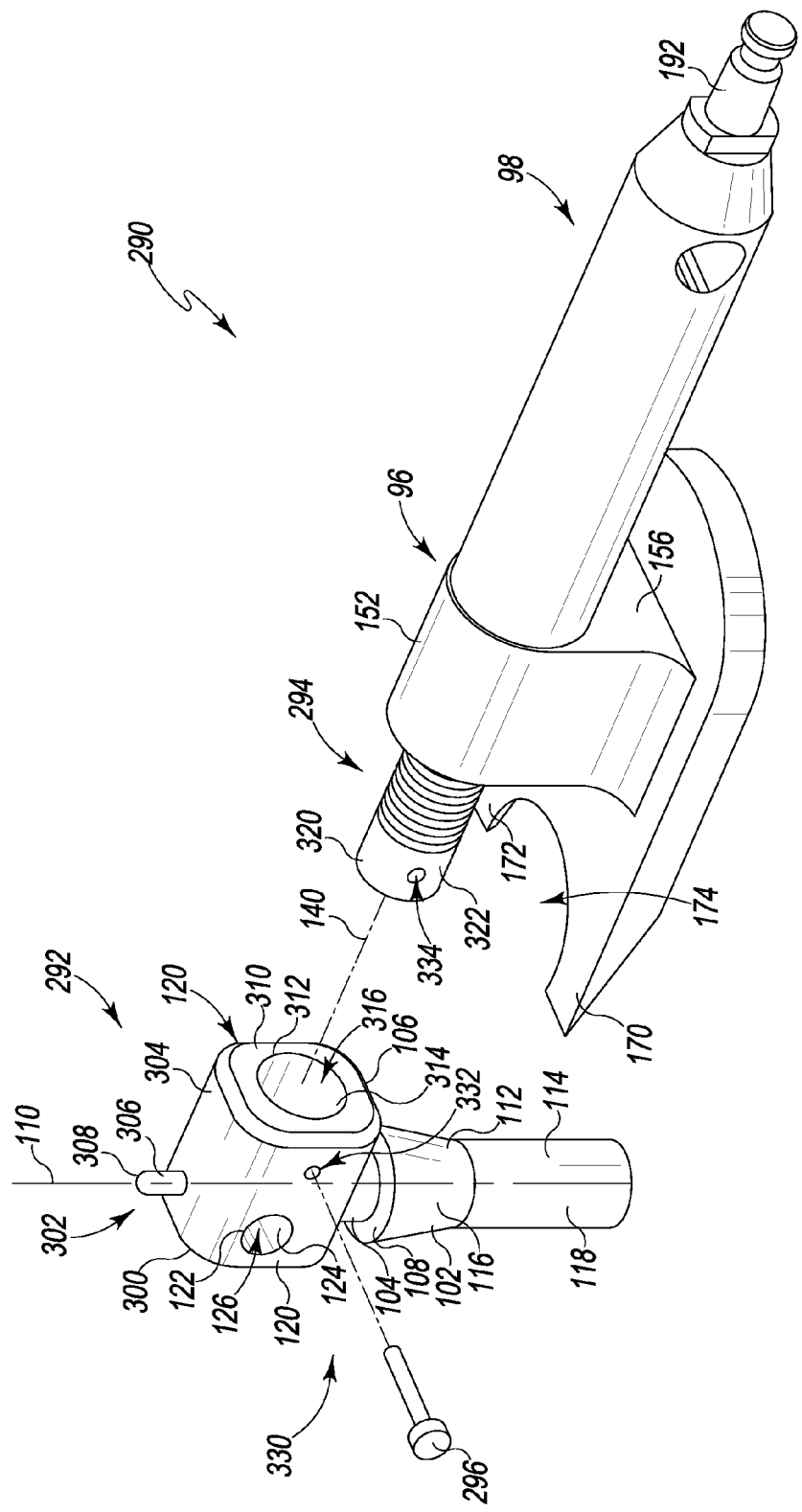
FIG. 9 a perspective view of another embodiment of an orthopaedic surgical instrument for use in disassembling the tibial component of FIG. 1.

Referring now to FIG. 9, another embodiment of a disassembly instrument (hereinafter instrument 290) is shown.

Some features of the embodiment illustrated in FIG. 9 are substantially similar to those described above in reference to the embodiment of FIGS. 1-8. Such features are designated in FIG. 9 with the same reference numbers as those used in FIGS. 1-8. Like the disassembly instrument described above in regard to FIGS. 1-8, the disassembly instrument 290 is configured to separate a tibial tray 20 from the sleeve 22 and facilitate the removal of the tibial component 14.

The instrument 290 includes an anchor 292 configured to be secured to a plurality of tibial trays of a plurality of tibial components, as described in greater detail below. The instrument 290 has a shaft 294 is removably coupled to the anchor 292 via a locking pin 296. The instrument 290 also includes a separator tool 96 configured to move relative to the anchor 292 and engage the tibial component to separate the tibial tray from the sleeve. An actuation collar 98 is attached to the shaft 294 and is operable to move the separator tool 96 along the shaft 294. In the illustrative embodiment, the components of the instrument 290 are formed from a metallic material such as, for example, steel, titanium alloy, cobalt chromium alloy, and so forth. It should be appreciated that in other embodiments the components may be formed from a hard polymeric material.

The anchor 292 of the instrument 290 includes a base 300, an engagement arm 102 configured to be positioned in the bore 36 defined in the tibial tray 20, and another engagement arm 302 configured to be positioned in a bore of another tibial tray (not shown). In the illustrative embodiment, the engagement arm 102 is secured to the base 100 via a connecting rod 104. As shown in FIG. 9, the connecting rod 104 extends between a bottom surface 106 of the base 100 and an upper surface 108 of the engagement arm 102. It should be appreciated that in other embodiments the engagement arm 102 may be secured directly to the base 100.

The engagement arm 102 has a longitudinal axis 110 that extends through an upper body 112 secured to the connecting rod 104 and a lower body 114 positioned below the upper body 112. In the illustrative embodiment, the upper body 112 has a frustoconical outer surface 116 shaped to match the tapered surface 38 that defines the proximal section 42 of the bore 36. When the anchor 92 is secured to the tibial tray 20, the upper body 112 of the arm 102 is received in the proximal section 42 of the bore 36 of the tibial tray 20. Additionally, the lower body 114 of the engagement arm 102 is received in the distal section 46 of the bore 36 when the anchor 292 is secured to the tibial tray 20. Similar to the upper body 112, the lower body 114 has a cylindrical outer surface 118 shaped to match the cylindrical surface 44 that defines the distal section 46 of the bore 36.

The base 300 of the anchor 292 includes a pair of side surfaces 120 that extend upwardly from the bottom surface 106. An opening 122 is defined in each side surface 120, and an inner wall 124 extends between the openings 122 to define a bore 126 through the base 300. The bore 126 is sized to receive a stabilizer rod 130, which may be used by the surgeon to support the instrument 90 on the patient's tibia 18.

As shown in FIG. 9, the base 300 has a top surface 304 that is positioned opposite the bottom surface 106. The engagement arm 302 extends upwardly from the top surface 304. The engagement arm 302 has a cylindrical body 306 and a tip 308 that are sized to be received in a bore defined in a tibial tray having a configuration different from that of the tibial tray 20. In that way, the instrument 290 may be to disassemble multiple types of tibial trays and sleeves. For example, in the illustrative embodiment, the tibial tray 20 is a mobile bearing tibial tray configured for use with a mobile tibial bearing, and, as described above, the engagement arm 102 is configured to be received in the bore 36 defined in the tray 20. A fixed bearing tibial tray configured for use with a fixed tibial bearing may be implanted in the patient's tibia, and the engagement arm 302 of the anchor 292 is configured to be received in a bore defined in the fixed bearing tibial tray.

The base 300 of the anchor 292 further includes another side surface 310 that extends upwardly from the bottom surface 106 between the side surfaces 120. The side surface 310 has an opening 312 defined therein, and an inner wall 314 extends inwardly from the opening 312 to define an aperture 316 in the base 300. The aperture 316 is sized to receive the end 320 of the shaft 294.

As shown in FIG. 9, the shaft 294 has a cylindrical body 322 extending from the end 320 to another end (not shown) positioned in the collar 98. The body 322 has a longitudinal axis 140 that extends orthogonal to the longitudinal axis 110 of the engagement arm 102. The body 322 has a cylindrical outer surface 142 that has a plurality of external threads 144 formed thereon, and the external threads 144 engage with the internal threads 202 of the collar 98 as described above in regard to FIGS. 1-8.

The anchor 292 of the instrument 290 is secured to the shaft 294 at a joint 330. The joint 330 includes the locking pin 296, which extends through a pair of openings 332 defined in the side surfaces 120 of the base 300 and a through-hole 334 defined in the cylindrical body 322 of the shaft 294. The pin 296 is removable from the openings 332 and through-hole 334 such that the anchor 292 be attached and detached from the shaft 294. In that way, the orientation of the engagement arms 102, 302 may be reversed such that the engagement arm 302 faces downward while the engagement arm 102 faces upward.

In operation, the disassembly instrument 290 may be used during an orthopaedic surgical procedure to facilitate the removal of a previously-implanted tibial component. If the tibial component includes the mobile bearing tibial tray 20, the surgeon may secure the anchor 292 to the shaft 294 in the orientation shown in FIG. 9. To do so, the surgeon may advance the base 300 over the shaft 294 such that the end 320 of the shaft 294 is positioned in aperture 316 of the base 300. The surgeon may then advance the pin 296 through the openings 332 defined in the base 300 and the through-hole 334 of the shaft 294, thereby securing the anchor 292 to the shaft 294.

If the tibial component includes a fixed bearing tibial tray, the surgeon may reverse the orientation of the anchor 292 such that the engagement arm 302 faces downward (i.e., opposite the orientation shown in FIG. 9). The surgeon may then secure to the anchor 292 to the shaft 294 in the manner described above. The surgeon may advance the base 300 over the shaft 294 such that the end 320 of the shaft 294 is positioned in aperture 316 of the base 300. The surgeon may then advance the pin 296 through the openings 332 defined in the base 300 and the through-hole 334 of the shaft 294, thereby securing the anchor 292 to the shaft 294. When assembled in either orientation, the instrument 290 may be used in a manner similar to that described above in regard to FIGS. 1-8 to remove an implanted tibial component from the patient's tibia.

While the disclosure has been illustrated and described in detail in the drawings and foregoing description, such an illustration and description is to be considered as exemplary and not restrictive in character, it being understood that only illustrative embodiments have been shown and described and that all changes and modifications that come within the spirit of the disclosure are desired to be protected.

There are a plurality of advantages of the present disclosure arising from the various features of the method, apparatus, and system described herein. It will be noted that alternative embodiments of the method, apparatus, and system of the present disclosure may not include all of the features described yet still benefit from at least some of the advantages of such features. Those of ordinary skill in the art may readily devise their own implementations of the method, apparatus, and system that incorporate one or more of the features of the present invention and fall within the spirit and scope of the present disclosure as defined by the appended claims.

The invention claimed is:

1. A method of performing an orthopaedic surgical procedure, comprising:

securing an anchor to a tibial prosthetic component implanted in a proximal end of a patient's tibia, the tibial prosthetic component including a tibial tray and a tibial sleeve secured to the tibial tray, moving a separator posteriorly toward the anchor to position a tip of the separator between a lower side of the tibial tray and an upper end of the tibial sleeve, advancing the separator from anterior to posterior between the lower side of the tibial tray and the upper end of the tibial sleeve to detach the tibial tray from the tibial sleeve, and removing the tibial tray from the proximal end of the patient's tibia.

2. The method of claim 1, further comprising positioning a cylindrical body of the anchor in an opening defined in the tibial tray.

3. The method of claim 1, wherein moving the separator toward the anchor includes sliding the separator along a shaft secured to the anchor.

4. The method of claim 3, wherein a collar is threaded onto the shaft, and sliding the separator along the shaft includes rotating the collar on the shaft to advance the collar along the shaft, and engaging the separator with the collar as the collar is advanced along the shaft.

5. The method of claim 4, further comprising engaging the collar with a handle, and operating the handle to rotate the collar on the shaft.

6. The method of claim 1, wherein advancing the separator includes positioning a wedge of the separator between the tibial tray and the tibial sleeve.

* * * * *